United States Patent
Wang et al.

(10) Patent No.: US 8,383,403 B2
(45) Date of Patent: Feb. 26, 2013

(54) RETICULOCYTE MIMETICS AND METHOD OF PREPARATION OF THE SAME

(75) Inventors: Lu Wang, Shenzhen (CN); Zuyue Xu, Shenzhen (CN); Tao Xia, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 378 days.

(21) Appl. No.: 12/774,442

(22) Filed: May 5, 2010

(65) Prior Publication Data

US 2010/0285560 A1     Nov. 11, 2010

(30) Foreign Application Priority Data

May 6, 2009   (CN) .......................... 2009 1 0107227

(51) Int. Cl.
*C12N 5/071* (2010.01)
(52) U.S. Cl. ............. 435/372; 435/2; 435/325; 435/366
(58) Field of Classification Search ........................ None
See application file for complete search history.

(56) References Cited

U.S. PATENT DOCUMENTS

| | | |
|---|---|---|
| 5,432,089 A | 7/1995 | Ryan et al. |
| 5,736,402 A | 4/1998 | Francis et al. |
| 5,858,789 A | 1/1999 | Francis et al. |
| 5,945,340 A | 8/1999 | Francis et al. |
| 6,399,388 B1 | 6/2002 | Ryan et al. |
| 6,406,915 B2 | 6/2002 | Ryan et al. |
| 6,444,471 B1 | 9/2002 | Johnson |
| 7,195,919 B2 | 3/2007 | Jacobs et al. |

*Primary Examiner* — James Martinell
(74) *Attorney, Agent, or Firm* — Kory D. Christensen; Matthew S. Bethards; Stoel Rives LLP (57) ABSTRACT

In one aspect of the present disclosure there is provided a method for preparing reticulocyte mimetics. In another aspect of the present disclosure there are provided reticulocyte mimetics obtained using the method. In yet another aspect of the present disclosure there is provided a whole blood reference control including the reticulocyte mimetics as provided. In still another aspect of the present disclosure there is provided a composition useful for preparing reticulocyte mimetics.

8 Claims, 5 Drawing Sheets

RETICULOCYTE MIMETICS AND METHOD OF PREPARATION OF THE SAME

RELATED APPLICATIONS

This application claims priority to Chinese Patent Application No. 200910107227.5, filed May 6, 2009, for "RETICULOCYTE MIMETICS AND METHOD OF PREPARATION OF THE SAME," the disclosure of which is fully incorporated herein by reference.

TECHNICAL FIELD

The present disclosure relates to the field of blood detection, more particularly to a hematology reference control.

BRIEF SUMMARY

The present disclosure relates to a hematology reference control. In particular, the present disclosure relates to a method for preparing reticulocyte mimetics, to reticulocyte mimetics obtained using said method, and to a whole blood hematology reference control comprising said reticulocyte mimetics.

DETAILED DESCRIPTION

A hematology reference control, as a liquid comprising single or multiple blood cell(s) or blood cell mimetic(s), has the same detectable characteristics as the blood, and thus is routinely used for monitoring the accuracy and precision of hematology analyzers.

The parameters related to reticulocytes are significant items of information that describe middle- and high-end blood cell analyzers. Reticulocytes are immature erythrocytes (red blood cells) that have the nucleus just extruded and still retain a small amount of RNA. Total reticulocyte count or reticulocyte percentage, one of the common parameters in hematology diagnosis, is of great value to the clinical diagnosis of anemia and the observation of the curative effect on this disorder. Naturally, accurate counting of reticulocytes by blood cell analyzers requires quality control of the reticulocyte count using a reference control.

U.S. Pat. Nos. 5,736,402, 5,858,789, 5,945,340 and 6,444,471 all disclose a method for preparing a reference control comprising reticulocyte mimetics. These methods comprise enriching and purifying reticulocytes in porcine blood by for example centrifugal settling, protecting the reticulocytes by a maturation-arrest approach, and then preserving the reticulocytes in a particular preserving solution. However, these methods suffer from serious drawbacks. Firstly, as the proportion of reticulocytes is low in porcine blood, a great amount of raw materials is needed. Secondly, as leukocytes and reticulocytes have a similar property of settling, they cannot be easily separated from each other using conventional approaches such as centrifugation. If a leukocyte filter is used, the low proportion of reticulocytes entails the use of a large number of leukocyte filters, which would greatly increase the cost of preparation. Finally, porcine reticulocytes are not good mimetics of human reticulocytes because the former are significantly smaller in volume than the latter.

U.S. Pat. No. 7,195,919 proposes a method for preparing a reference control that simulates reticulocytes, said method primarily comprising linking biological high polymers such as nucleic acids, peptide nucleic acids and mucopolysaccharides to the surface of mammal erythrocytes and subjecting the linked high polymers to and binding with a dye, in order to simulate the morphology of reticulocytes in instrumental detection. The principle behind the method is linking of nucleic acids to a cell surface, but it is hard to ensure the linking strength (particularly during long-term storage). Moreover, it is necessary to activate the nucleic acids and then remove the activating reagent. Therefore, the execution of this method is complicated and hardly controllable.

In U.S. Pat. Nos. 6,399,388, 6,406,915, and 5,432,089, the simulation of the morphology of reticulocytes is achieved by swelling the cell membrane of erythrocytes by varying the osmotic pressure to produce pores in the membrane, and then infusing nucleic acids, e.g. RNA, or polyanions into the cells. The approaches adopted in these patents also suffer from various problems. Firstly, the proportion of the erythrocytes into which nucleic acids are infused is not high, resulting in a low productivity of simulated reticulocytes. Thus, a mixture of erythrocytes and quasi reticulocytes is finally obtained. Secondly, the cells have decreased membrane strength after being subjected to swelling to produce pores. Thirdly, the execution of these methods is complicated, making it difficult to use these methods for producing reference control products.

Therefore, an alternative reticulocyte mimetics and method of preparation of the same is provided in this disclosure.

In one aspect of the present disclosure there is provided a method for preparing reticulocyte mimetics, the method comprising the following steps of:

washing an anticoagulant blood sample containing anucleate erythrocytes and separating the anucleate erythrocytes therein to obtain purified anucleate erythrocytes;

adding a cell treatment solution and a fixing agent to the purified anucleate erythrocytes to treat and fix substances on a surface of and/or inside the anucleate erythrocytes, the cell treatment solution comprising a protein denaturing agent and optionally a permeate agent and/or a surfactant; and washing the obtained reticulocyte mimetics product.

In another aspect of the present disclosure there are provided reticulocyte mimetics which can be prepared by the above method.

In yet another aspect of the present disclosure there is provided a whole blood reference control, which includes the reticulocyte mimetics prepared by the above method.

In still another aspect of the present disclosure there is provided a composition useful for preparing reticulocyte mimetics, the composition comprising a cell treatment solution and a fixing agent, the cell treatment solution comprising a protein denaturing agent and optionally a permeate agent and/or a surfactant. The composition can be used in the method for preparing reticulocyte mimetics.

The method of simulating reticulocytes by treating anucleate erythrocytes with a cell treatment solution, as disclosed in the present disclosure, may avoid the use of nucleic acids or similar biopolymers, may be simple in execution and cost-effective, therefore allowing easy industrial production of a hematology reference control.

Other aspects of the present disclosure will become apparent upon reading the following detailed description of the present disclosure.

In one embodiment of the present disclosure, there is provided a method for preparing reticulocyte mimetics using anucleate erythrocytes. These anucleate erythrocytes are from human or animal. Particular reagents are then added to treat and fix the cell surface and intracellular substances of these anucleate erythrocytes to render the cells adsorptive to nucleic acid dyes, such as fluorescent detection dyes, thereby obtaining simulated reticulocytes.

The method comprises the following steps of:

washing an anticoagulant blood sample containing anucleate erythrocytes and separating the anucleate erythrocytes therein to obtain purified anucleate erythrocytes;

adding a cell treatment solution and a fixing agent to the purified anucleate erythrocytes to treat and fix the substances on a surface of and/or inside the anucleate erythrocytes, the cell treatment solution comprising a protein denaturing agent and optionally a permeate agent and/or surfactant; and washing the obtained reticulocyte mimetics product.

In one embodiment of the present disclosure, purified anucleate erythrocytes are obtained by removing blood plasma and platelets, etc. by way of, e.g., centrifugation or standing of the blood and then removing leukocytes by a leukocyte filter or other equivalent means.

The blood sample isolated from any human or animal blood containing anucleate erythrocytes maybe viable in embodiments of the present disclosure. Animal anucleate erythrocytes that have a similar mean corpuscular volume (MCV) to that of human anucleate erythrocytes can be used to prepare reticulocyte mimetics according to the method of the present disclosure. Typically, human or mammal blood is viable, particularly fresh blood that will give a better result.

Subsequently, the result purified anucleate erythrocytes are chemically treated by adding a cell treatment solution comprising, inter alia, a protein denaturing agent and optionally a permeate agent and/or a surfactant to treat the cell components. Then a suitable fixing agent is added to fix the cell membrane of the anucleate erythrocytes whose properties have been altered, so as to increase the stability of the cells.

It is well known that those macromolecular compounds (e.g., protein molecules) comprise both polar groups (hydrophilic groups) and non-polar groups (hydrophobic groups), when they are present in a polar solvent (such as water), their polar groups (hydrophilic groups) are exposed to the exterior of the molecular spatial structure, while their non-polar groups (hydrophobic groups) are hid inside the molecular spatial structure.

Without wishing to be bound by any theory, the protein denaturing agent useful in the present disclosure functions to alter the spatial structure of the macromolecular compounds (such as protein molecules) on and/or in the membrane of the erythrocytes or inside the erythrocytes, so that the hydrophobic groups originally hid inside the molecular structure are exposed to permit the erythrocytes to bind with nucleic acid dyes, such as fluorescent detection dyes, thus simulating reticulocytes.

Therefore it will be appreciated by one skilled in the art that any denaturing agent can be used as the denaturing agent according to the present disclosure so long as it can alter the molecular structure of proteins as described above. For example, denaturing agents useful in the present disclosure can be guanidine hydrochloride, guanidinium isothiocyanate, urea or ammonium sulfate, or any combination thereof.

The final concentration of the protein denaturing agent in use can be in the range of 0.01-10% (w/v). For example, the protein denaturing agent may be selected from anyone of guanidine hydrochloride in a final concentration in the range of 0.05%-10% (w/v), guanidinium isothiocyanate in a final concentration in the range of 0.01%-5% (w/v), urea in a final concentration in the range of 0.01%-10% (w/v), or any combination thereof.

Without wishing to be bound by any theory, the fixing agent useful in the present disclosure not only fixes the cell structure but also stabilizes the spatial structure of the structurally denatured protein molecules, so that the reticulocyte mimetics prepared can remain stable over a period of time to allow for accurate detection.

Therefore, it is understood by those skilled in the art that commonly used cell fixing agents, such as acetone, oxalaldehyde, pyruvaldehyde, succinaldehyde, glutaraldehyde, paraformaldehyde, formaldehyde and ethanol, or any combination thereof, can be used as the fixing agent according to the present disclosure.

The concentration of the fixing agent used in the present disclosure can be determined by one skilled in the art according to specific conditions, such as reagents used and time of action. For example, the final concentration of the fixing agent in use can be in the range of 0.005-8% (v/v), or 0.005-5% (w/v). For example, the fixing agent may be selected from any one of acetone in a final concentration in the range of 0.005%-3% (v/v), glacial acetic acid in a final concentration in the range of 0.005%-2% (v/v), picric acid in a final concentration in the range of 0.005%-3% (w/v), glyoxal in a final concentration in the range of 0.005%-5% (v/v), pyruvaldehyde in a final concentration in the range of 0.01%-3% (v/v), succinaldehyde in a final concentration in the range of 0.005%-5% (v/v), glutaraldehyde in a final concentration in the range of 0.005%-8% (v/v), paraformaldehyde in a final concentration in the range of 0.005%-3% (w/v), formaldehyde in a final concentration in the range of 0.01%-5% (v/v), ethanol in a final concentration in the range of 0.005%-5% (v/v), or any combination thereof.

The time of action of the fixing agent varies depending on the identity and concentration of the fixing agent used, and may be typically 1-8 hours. However, it is appreciated by those skilled in the art that the concentration of the fixing agent is correlated with time of action in such a manner that the higher the concentration, the shorter the time of action. In any event, it is well within the skill of those skilled in the art to choose a suitable concentration and time of action of the fixing agent according to specific conditions of the action.

The cell treatment solution disclosed in the present disclosure optionally comprises a permeate agent. Without wishing to be bound by any theory, the permeate agent useful in the present disclosure facilitates the entry of other reagents used according to the present disclosure (such as the denaturing agent and the fixing agent) into the cells to interact with relevant intracellular substances. Therefore it will be appreciated by one skilled in the art that the permeate agent useful in the present disclosure can be any reagent having a cell membrane permeation effect, such as dimethylsulfoxide, glycerol, ethylene glycol, propylene glycol, formamide and acetamide, or any combination thereof.

The final concentration of the permeate agent in use can be in the range of 0.1-30% (v/v). For example, the permeate agent can be dimethylsulfoxide in a final concentration in the range of 0.1%-20% (v/v), glycerol in a final concentration in the range of 0.5%-25% (v/v), ethylene glycol in a final concentration in the range of 1%-30% (v/v), propylene glycol in a final concentration in the range of 1%-30% (v/v), formamide in a final concentration in the range of 0.1%-20% (v/v), or acetamide in a final concentration in the range of 0.1%-20% (v/v), or any combination thereof.

The cell treatment solution disclosed in the present disclosure optionally comprises a surfactant. The surfactant useful in the present disclosure can be any cationic surfactant, anionic surfactant and nonionic surfactant commonly used in the art.

The cationic surfactant useful in the present disclosure may be for example a quaternary ammonium-type cationic surfactant having the following general formula:

wherein $R_1$, $R_2$ and $R_3$ are each independently selected from hydrogen atom, $C_1$-$C_8$alkyl and $C_6$-$C_{20}$aralkyl; $R_4$ is selected from $C_8$-$C_{18}$ alkyl, $C_{8-18}$alkenyl and $C_6$-$C_{18}$aralkyl; X is selected from halogen, sulphate, and sulphonate anions.

For example, the cationic surfactant useful in the present disclosure can be hexadecyl trimethyl ammonium chloride or dodecyltrimethylammonium chloride.

The anionic surfactant useful in the present disclosure may be for example a sulphonate having the formula of R—SO$_3$Na, wherein R is $C_8$-$C_{20}$alkyl. For example, the anionic surfactant useful in the present disclosure can be sodium dodecyl sulphonate.

The nonionic surfactant useful in the present disclosure may be for example a polyoxyethylene-type nonionic surfactant having the following general formula:

wherein $R_1$ is selected from H, $C_{1-22}$alkyl and $C_{2-22}$alkenyl; A is selected from —O—, —COO— and -ph-O—; and n is an integer of 10-1000. A specific compound may be, for example, polyethylene glycol, particularly polyethylene glycol having a molecular weight in the range of 6000-20000.

Combinations of the various surfactants can also be used.

The final concentration of the surfactant in use can be in the range of 0.005-5% (w/v). For example, the surfactant can be polyethylene glycol in a final concentration in the range of 0.005%-5% (w/v), sodium dodecyl sulphonate in a final concentration in the range of 0.005%-5% (w/v), or hexadecyl trimethyl ammonium chloride in a final concentration in the range of 0.005%-3% (w/v), or any combination thereof.

The neutral isotonic buffers commonly used by those skilled in the art can be used in the washing step according to the present disclosure. For example, the washing solutions that can be used include a neutral isotonic phosphate buffer, a neutral isotonic borate buffer, a neutral isotonic citrate buffer, and a neutral isotonic NaCl solution.

The anticoagulant agents useful in the present disclosure are those commonly used clinically. For example, 1.5% (W/N) EDTA-2Na or EDTA-2K neutral isotonic anticoagulant agent or 1% (W/N) sodium citrate neutral isotonic anticoagulant agent can be used.

The preserving solutions useful in the present disclosure are those cell preserving solutions commonly used in the art.

The sequence in which the cell treatment solution and the fixing agent are added can be varied. Generally, it is desired that the action of the cell treatment solution on the membrane and intracellular substances of erythrocytes is completed before the molecular structure of proteins is stabilized by the fixing agent. Therefore, commonly, the cell treatment solution is first added to treat the cells for a period of time prior to addition of the fixing agent. However, the cell treatment solution and the fixing agent can also be added simultaneously. Further, the fixing agent can be first added to react for a short period of time followed by addition of the cell treatment solution (or alternatively, the concentration of the fixing agent is decreased and then the diluted fixing agent is first added to react for some time followed by addition of the cell treatment solution). It is appreciated by those skilled in the art that all these choices of addition sequence are all within the scope of the present disclosure. It is exemplary that the cell treatment solution is added first to treat the cells for a period of time, then the fixing agent is added.

The prepared reticulocyte mimetics product is washed by a suitable washing solution.

In the one embodiment of the present disclosure, the reticulocyte mimetics prepared are optionally stored in a preserving solution.

The preserving solution useful in the method of the present disclosure may be a solution that can preserve the cells for a long time. Any cell preserving solutions known to those skilled in the art can be used.

In another aspect of the present disclosure, there are provided reticulocyte mimetics prepared using the method disclosed in the present disclosure.

Figure 1:
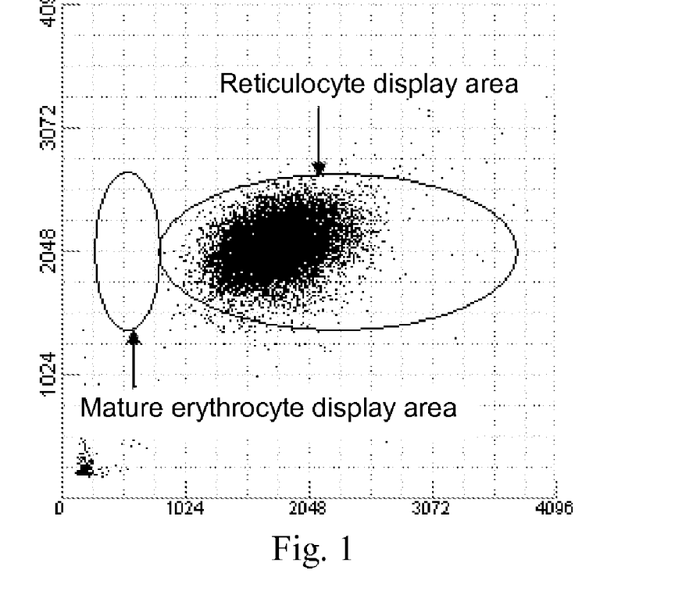
FIG. 1 shows a diagram of the reticulocyte mimetics prepared by a method disclosed in the present disclosure, being detected on a blood cell analyzer whose principle of detection is based on fluorescent staining of nucleic acids (only reticulocytes are shown, RET channel for short), wherein the abscissa represents fluorescence intensity, the ordinate represents forward scattered light intensity, and the black scattered points represent reticulocyte mimetics.

Mature erythrocytes contain no nucleic acids, so they do not bind with the fluorescent detection dye for reticulocytes. In the method provided in the present disclosure, the surface or intracellular substances of anucleate erthrocytes are modified to be adsorptive to fluorescent dyes so that the cells can effectively adsorb or bind with the fluorescent dye during instrumental detection and generate detectable fluorescence signals under the excitation of a laser light source. Eventually, a cell group is observed that is markedly distinguished from mature erythrocytes and is falling in the display area of reticulocytes, as shown in FIG. 1. If the reticulocyte mimetics prepared are mixed in a certain proportion with mature erythrocytes and the mixture is subjected to detection on the blood cell analyzer whose principle of detection is based on fluorescent staining of nucleic acids, two cell groups having distinct boundaries are observed, one in the mature erythrocyte area and the other in the reticulocyte area, thus achieving the quality control of reticulocyte count.

In yet another aspect of the present disclosure, there is provided a blood reference control containing the reticulocyte mimetics disclosed in the present disclosure. The reticulocyte mimetics prepared according to the method disclosed in the present disclosure can be mixed with mimetics for erythrocytes, leukocytes, platelets or other blood cells to form a reference control for the multi-parameter blood cell analyzer whose principle of detection is based on fluorescent staining of nucleic acids. The ratio of reticulocytes to erythrocytes can be effectively adjusted.

In still another aspect of the present disclosure, there is provided a composition useful for preparing reticulocyte mimetics, the composition comprising a cell treatment solution and a fixing agent, the cell treatment solution comprising a protein denaturing agent and optionally a permeate agent and/or a surfactant. The composition disclosed can be used in the method disclosed for preparing reticulocyte mimetics.

EXAMPLES

The present disclosure will now be described in further details by way of examples which are illustrative of the present disclosure and are not intended to be limiting in any sense.

The reagents used in the examples are as follows. The chemicals used in the preparation of the reagents are analytically pure unless specifically stated otherwise.

Anticoagulant agent: 15 g of EDTA-$Na_2$ in 1 L of distilled water. The pH is adjusted to 7.0±0.2 with HCl or NaOH, and the osmotic pressure is adjusted to 300±20 mOsm/kg$H_2$O with NaCl.

Washing solution: 8.5 g of NaCl, 2.2 g of $Na_2HPO_4$ and 0.4 g of $NaH_2PO_4$ in 1 L of distilled water. The pH is adjusted to 7.0±0.2 with HCl or NaOH, and the osmotic pressure is adjusted to 300±20 mOsm/kg$H_2$O with NaCl.

Cell treatment solution A: 5 mL of deionized formamide, 5 g of urea, 0.5 g of sodium dodecyl sulphonate and 9 g of NaCl in 1 L of distilled water. The pH is adjusted to 7.0±0.1 with HCl or NaOH after homogeneous mixing.

Cell treatment solution B: 5 mL of dimethylsulfoxide, 20 mL of propylene glycol, 5 g of guanidine hydrochloride, 0.5 g of dodecyltrimethylammonium chloride and 9 g of NaCl in 1 L of distilled water. The pH is adjusted to 7.0±0.1 with HCl or NaOH after homogeneous mixing.

Cell treatment solution C: 10 mL of glycerol, 5 g of guanidinium isothiocyanate, 0.5 g of polyethylene glycol 20000 and 9 g of NaCl in 1 L of distilled water. The pH is adjusted to 7.0±0.1 with HCl or NaOH after homogeneous mixing.

Cell treatment solution D: 20 mL of propylene glycol, 5 g of guanidine hydrochloride, 0.1 g of hexadecyl trimethyl ammonium chloride and 9 g of NaCl in 1 L of distilled water. The pH is adjusted to 7.0±0.1 with HCl or NaOH after homogeneous mixing.

Cell treatment solution E: 5 mL of dimethylsulfoxide, 5 g of guanidine hydrochloride and 9 g of NaCl in 1 L of distilled water. The pH is adjusted to 7.0±0.1 with HCl or NaOH after homogeneous mixing.

Cell treatment solution F: 5 g of urea, 0.5 g of polyethylene glycol 20000 and 9 g of NaCl in 1 L of distilled water. The pH is adjusted to 7.0±0.1 with HCl or NaOH after homogeneous mixing.

Cell treatment solution G: 5 g of urea and 9 g of NaCl in 1 L of distilled water. The pH is adjusted to 7.0±0.1 with HCl or NaOH after homogeneous mixing.

Fixing agent A: 100 mL of glutaraldehyde (25%), 20 mL of glacial acetic acid and 30 mL of picric acid are mixed homogeneously at room temperature and then the mixture is added with distilled water to make up 1 L.

Fixing agent B: 300 mL of formaldehyde (37%), 40 mL of glutaraldehyde (25%), 10 mL of ethanol and 5 mL of acetone are mixed homogeneously at room temperature and then the mixture is added with distilled water to make up 1 L.

Preserving solution: 9.0 g of glucose, 5.0 g of mannitol, 1.3 g of ammonium chloride, 10.0 g of glycine, 0.14 g of adenine, 2.2 g of dibasic sodium phosphate, 0.4 g of monobasic sodium phosphate, 1.0 g of streptomycin sulfate, 200,000 units of penicillin in 1 L of distilled water. The pH is adjusted to 7.0±0.1 with HCl or NaOH after homogeneous mixing, and the osmotic pressure is adjusted to 300±10 mOsm/kg$H_2$O with NaCl.

Formulation of Full-Component Reference Controls

The reticulocyte mimetics prepared in the following Examples 1-8 were mixed with erythrocyte mimetics, platelet mimetics, and leukocyte mimetics in a suitable amount of preserving solution to formulate full-component reference controls with different parameter levels according to the following Table. These controls can be used for the daily quality control of the BC series flow cytometers with a detection wavelength of 635 nm manufactured by Shenzhen Mindray Bio-Medical Electronics Co. Ltd (Shenzhen, People's Republic of China).

TABLE

| Parameters | Low value control | Middle value control | High value control |
|---|---|---|---|
| WBC ($10^9$/L) | 3.35-4.40 | 6.60-8.20 | 17.00-23.00 |
| RBC ($10^{12}$/L) | 2.20-2.80 | 4.00-5.00 | 5.23-5.83 |
| RET % | 5.90-11.90 | 2.20-6.20 | 0.30-1.30 |
| PLT ($10^9$/L) | 60-90 | 150-300 | 420-560 |

Example 1

Figure 2:
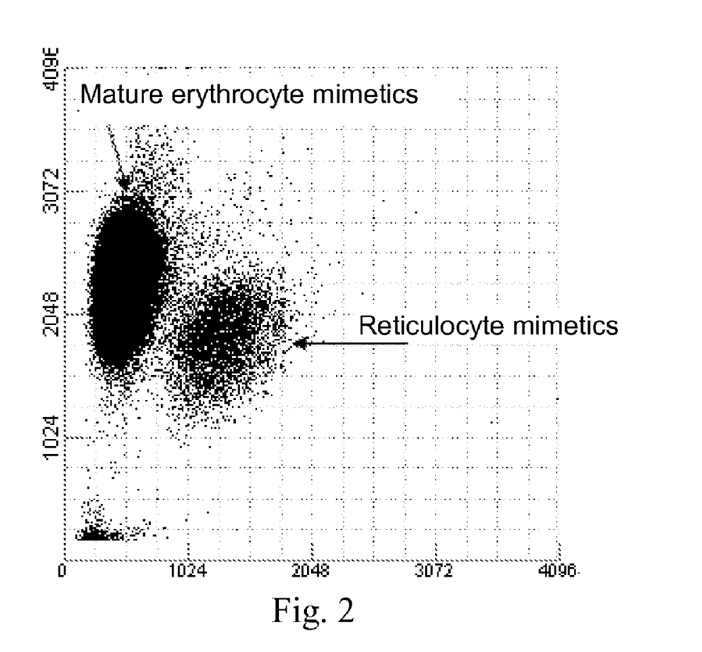
FIG. 2 shows a diagram of a whole blood reference control for use in a hematology analyzer formulated by mixing the reticulocyte mimetics prepared in Example 1 in a certain proportion with other blood cell mimetics, being detected on the blood cell analyzer whose principle of detection is based on fluorescent staining of nucleic acids (only RET channel is shown), wherein the abscissa represents fluorescence intensity and the ordinate represents forward scattered light intensity.

Fresh anticoagulant bovine whole blood was collected which comprised 200 mL of anticoagulant agent for every 800 mL of bovine blood. The anticoagulant whole blood was centrifuged at 2400 rpm for 5 minutes. The supernatant was discarded and the pellet was washed with washing solution followed by further centrifugation at 2400 rpm for 5 minutes. Washing was repeated for one or two times. The supernatant was discarded, and the leukocytes were removed using a leukocyte filter. The filtrate was adjusted to an erythrocyte concentration of $1\times10^{12}$ cells/L using cell treatment solution A and stirred to homogeneity for 1-5 minutes. Fixing agent A was added to a final concentration of 2% (the volume ratio of the fixing agent to the total reaction solution; the same in the following examples) and reaction was allowed for 5 hours at room temperature while the mixture was constantly stirred to homogeneity. The reaction product was repeatedly washed with washing solution for three or four times. The product was suspended in a suitable amount of preserving solution, and the suspension was mixed in a certain proportion with other cell mimetics to formulate a hematology reference control for a blood cell analyzer, as described in the foregoing Section "Formulation of Full-Component Reference Controls". The reference control obtained was detected on the blood cell analyzer whose principle of detection is based on fluorescent staining of nucleic acids. The result is as shown in FIG. 2 (only the diagram on the RET channel is shown).

Example 2

Figure 3:
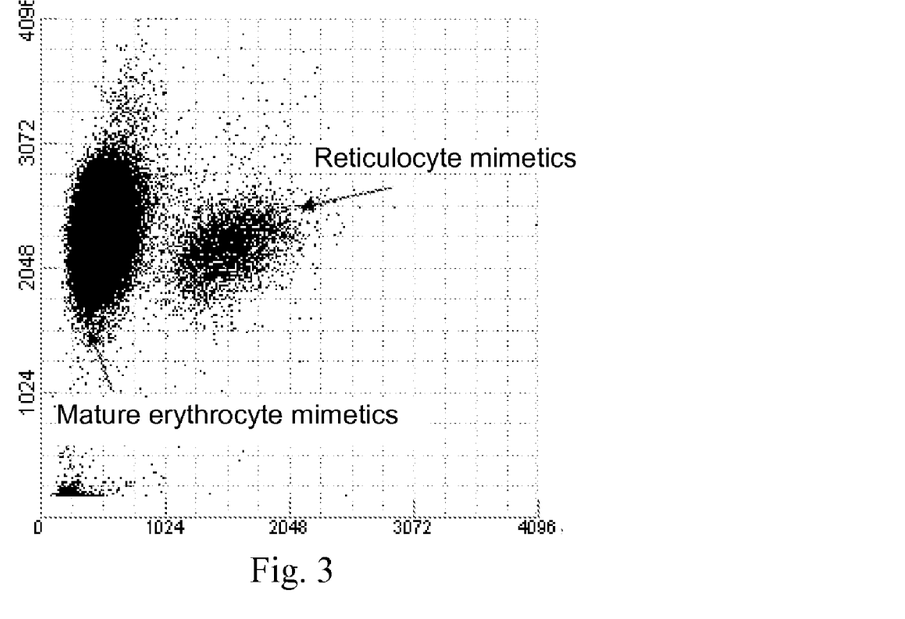
FIG. 3 shows a diagram of a whole blood reference control for use in a hematology analyzer formulated by mixing the reticulocyte mimetics prepared in Example 2 in a certain proportion with other blood cell mimetics, being detected on the blood cell analyzer whose principle of detection is based on fluorescent staining of nucleic acids (only RET channel is shown), wherein the abscissa represents fluorescence intensity and the ordinate represents forward scattered light intensity.

Fresh anticoagulant human whole blood was collected. The anticoagulant whole blood was centrifuged at 2400 rpm for 5 minutes. The supernatant was discarded and the pellet was washed with washing solution followed by further centrifugation at 2400 rpm for 5 minutes. Washing was repeated for one or two times. The supernatant was discarded, and the leukocytes were removed using a leukocyte filter. The filtrate was adjusted to an erythrocyte concentration of $1\times10^{12}$ cells/L using cell treatment solution B and stirred to homogeneity for 1-5 minutes. Fixing agent A was added to a final concentration of 2% and reaction was allowed for 5 hours at room temperature while the mixture was constantly stirred to homogeneity. The reaction product was repeatedly washed with the washing solution for three or four times. The product was suspended in a suitable amount of preserving solution, and the suspension was mixed in a certain proportion with other cell mimetics to formulate a hematology reference control for a blood analyzer, as described in the foregoing Section "Formulation of Full-Component Reference Controls". The reference control obtained was detected on the blood cell analyzer whose principle of detection is based on fluorescent staining of nucleic acids. The result is as shown in FIG. 3 (only the diagram on the RET channel is shown).

Example 3

Figure 4:
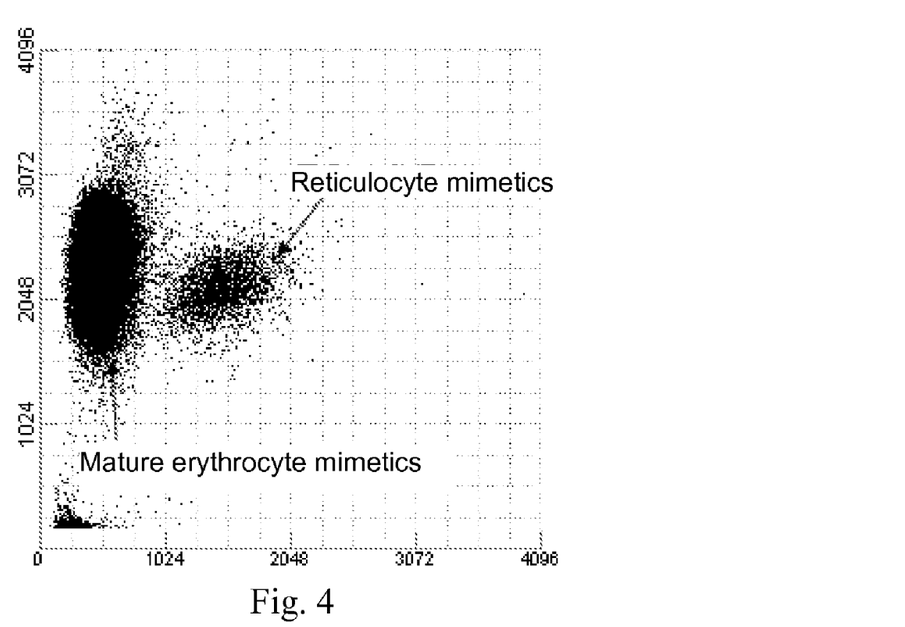
FIG. 4 shows a diagram of a whole blood reference control for use in a hematology analyzer formulated by mixing the reticulocyte mimetics prepared in Example 3 in a certain proportion with other blood cell mimetics, being detected on the blood cell analyzer whose principle of detection is based on fluorescent staining of nucleic acids (only RET channel is shown), wherein the abscissa represents fluorescence intensity and the ordinate represents forward scattered light intensity.

Fresh anticoagulant human whole blood was collected. The anticoagulant whole blood was centrifuged at 2400 rpm for 5 minutes. The supernatant was discarded and the pellet was washed with washing solution followed by further centrifugation at 2400 rpm for 5 minutes. Washing was repeated for one or two times. The supernatant was discarded, and the leukocytes were removed using a leukocyte filter. The filtrate was adjusted to an erythrocyte concentration of $1\times10^{12}$ cells/L using cell treatment solution C and stirred to homogeneity for 1-5 minutes. Fixing agent A was added to a final concentration of 8% and reaction was allowed for 2 hours at 4° C. while the mixture was constantly stirred to homogeneity. The reaction product was repeatedly washed with the washing solution for three or four times. The product was suspended in a suitable amount of preserving solution, and the suspension was mixed in a certain proportion with other cell mimetics to formulate a hematology reference control for a blood analyzer, as described in the foregoing Section "Formulation of Full-Component Reference Controls". The reference control obtained was detected on the blood cell analyzer whose principle of detection is based on fluorescent staining of nucleic acids. The result is as shown in FIG. 4 (only the diagram on the RET channel is shown).

Example 4

Figure 5:
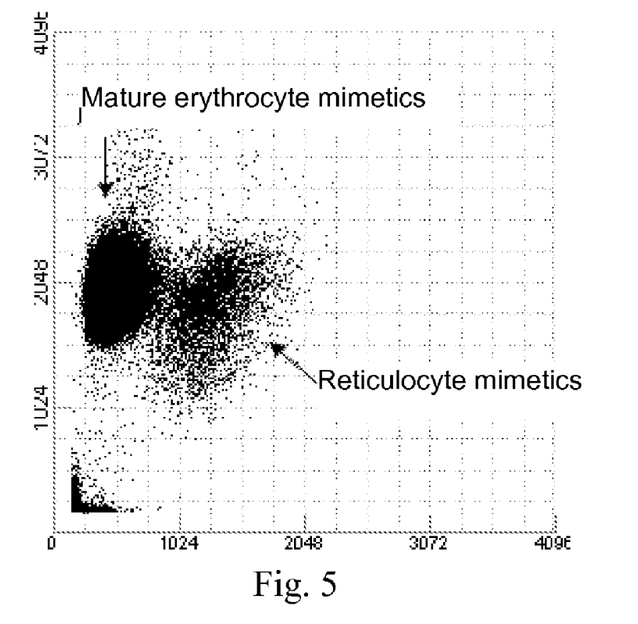
FIG. 5 shows a diagram of a whole blood reference control for use in a hematology analyzer formulated by mixing the reticulocyte mimetics prepared in Example 4 in a certain proportion with other blood cell mimetics, being detected on the blood cell analyzer whose principle of detection is based on fluorescent staining of nucleic acids (only RET channel is shown), wherein the abscissa represents fluorescence intensity and the ordinate represents forward scattered light intensity.

Fresh anticoagulant human whole blood was collected. The anticoagulant whole blood was centrifuged at 2400 rpm for 5 minutes. The supernatant was discarded and the pellet was washed with washing solution followed by further centrifugation at 2400 rpm for 5 minutes. Washing was repeated for one or two times. The supernatant was discarded, and the leukocytes were removed using a leukocyte filter. The filtrate was adjusted to an erythrocyte concentration of $1\times10^{12}$ cells/L using cell treatment solution D and stirred to homogeneity for 1-5 minutes. Fixing agent A was added to a final concentration of 0.2% and reaction was allowed for 5 hours at 37° C. while the mixture was constantly stirred to homogeneity. The reaction product was repeatedly washed with washing solution for three or four times. The product was suspended in a suitable amount of preserving solution, and the suspension was mixed in a certain proportion with other cell mimetics to formulate a hematology reference control for a blood analyzer, as described in the foregoing Section "Formulation of Full-Component Reference Controls". The reference control obtained was detected on the blood cell analyzer whose principle of detection is based on fluorescent staining of nucleic acids. The result is as shown in FIG. 5 (only the diagram on the RET channel is shown).

Example 5

Figure 6:
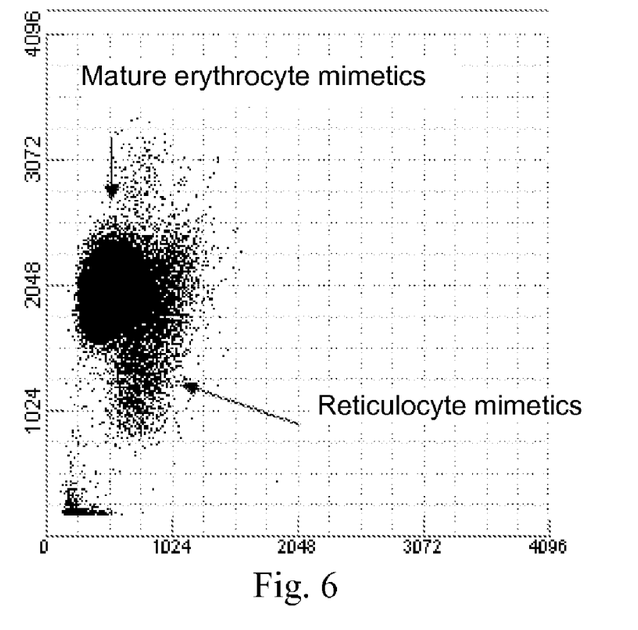
FIG. 6 shows a diagram for a whole blood reference control for use in a hematology analyzer formulated by mixing the reticulocyte mimetics prepared in Example 5 in a certain proportion with other blood cell mimetics, being detected on the blood cell analyzer whose principle of detection is based on fluorescent staining of nucleic acids (only RET channel is shown), wherein the abscissa represents fluorescence intensity and the ordinate represents forward scattered light intensity.

Fresh anticoagulant human whole blood was collected. The anticoagulant whole blood was centrifuged at 2400 rpm for 5 minutes. The supernatant was discarded and the pellet was washed with washing solution followed by further centrifugation at 2400 rpm for 5 minutes. Washing was repeated for one or two times. The supernatant was discarded, and the leukocytes were removed using a leukocyte filter. The filtrate was adjusted to an erythrocyte concentration of $1\times10^{12}$ cells/L using cell treatment solution E and stirred to homogeneity for 1-5 minutes. Fixing agent A was added to a final concentration of 2% and reaction was allowed for 5 hours at room temperature while the mixture was constantly stirred to homogeneity. The reaction product was repeatedly washed with washing solution for three or four times. The product was suspended in a suitable amount of preserving solution, and the suspension was mixed in a certain proportion with other cell mimetics to formulate a hematology reference control for a blood analyzer, as described in the foregoing Section "Formulation of Full-Component Reference Controls". The reference control obtained was detected on the blood cell analyzer whose principle of detection is based on fluorescent staining of nucleic acids. The result is as shown in FIG. 6 (only the diagram on the RET channel is shown).

Example 6

Figure 7:
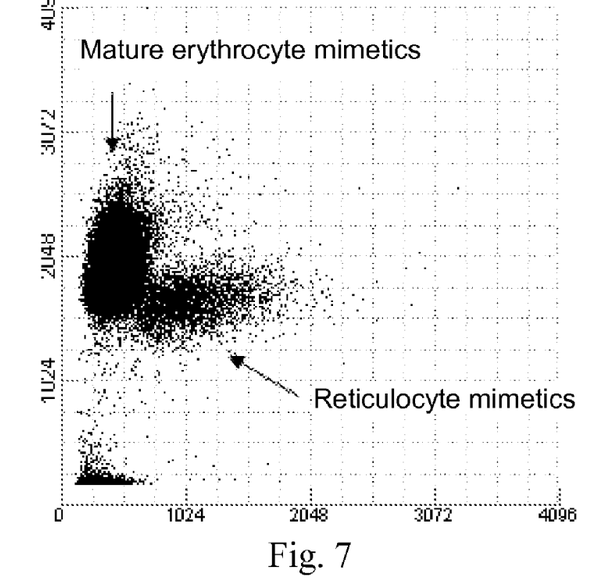
FIG. 7 shows a diagram for a whole blood reference control for use in a hematology analyzer formulated by mixing the reticulocyte mimetics prepared in Example 6 in a certain proportion with other blood cell mimetics, being detected on the blood cell analyzer whose principle of detection is based on fluorescent staining of nucleic acids (only RET channel is shown), wherein the abscissa represents fluorescence intensity and the ordinate represents forward scattered light intensity.

Fresh anticoagulant human whole blood was collected. The anticoagulant whole blood was centrifuged at 2400 rpm for 5 minutes. The supernatant was discarded and the pellet was washed with washing solution followed by further centrifugation at 2400 rpm for 5 minutes. Washing was repeated for one or two times. The supernatant was discarded, and the leukocytes were removed using a leukocyte filter. The filtrate was adjusted to an erythrocyte concentration of $1\times10^{12}$ cells/L using cell treatment solution F and stirred to homogeneity for 1-5 minutes. Fixing agent A was added to a final concentration of 2% and reaction was allowed for 5 hours at room temperature while the mixture was constantly stirred to homogeneity. The reaction product was repeatedly washed with washing solution for three or four times. The product was suspended in a suitable amount of preserving solution, and the suspension was mixed in a certain proportion with other cell mimetics to formulate a hematology reference control for a blood analyzer, as described in the foregoing Section "Formulation of Full-Component Reference Controls". The reference control obtained was detected on the blood cell analyzer whose principle of detection is based on fluorescent staining of nucleic acids. The result is as shown in FIG. 7 (only the diagram on the RET channel is shown).

Example 7

Figure 8:
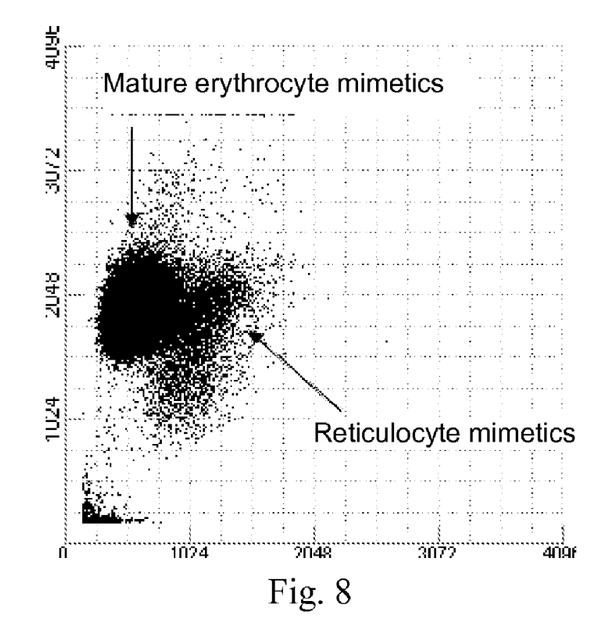
FIG. 8 shows a diagram for a whole blood reference control for use in a hematology analyzer formulated by mixing the reticulocyte mimetics prepared in Example 7 in a certain proportion with other blood cell mimetics, being detected on the blood cell analyzer whose principle of detection is based on fluorescent staining of nucleic acids (only RET channel is shown), wherein the abscissa represents fluorescence intensity and the ordinate represents forward scattered light intensity.

Fresh anticoagulant human whole blood was collected. The anticoagulant whole blood was centrifuged at 2400 rpm for 5 minutes. The supernatant was discarded and the pellet was washed with washing solution followed by further centrifugation at 2400 rpm for 5 minutes. Washing was repeated for one or two times. The supernatant was discarded, and the leukocytes were removed using a leukocyte filter. The filtrate was adjusted to an erythrocyte concentration of $1\times10^{12}$ cells/L using cell treatment solution G and stirred to homogeneity for 1-5 minutes. Fixing agent A was added to a final concentration of 2% and reaction was allowed for 5 hours at room temperature while the mixture was constantly stirred to homogeneity. The reaction product was repeatedly washed with washing solution for three or four times. The product was suspended in a suitable amount of preserving solution, and the suspension was mixed in a certain proportion with other cell mimetics to formulate a hematology reference control for a blood analyzer, as described in the foregoing Section "Formulation of Full-Component Reference Controls". The reference control obtained was detected on the blood cell analyzer whose principle of detection is based on fluorescent staining of nucleic acids. The result is as shown in FIG. 8 (only the diagram on the RET channel is shown).

Example 8

Figure 9:
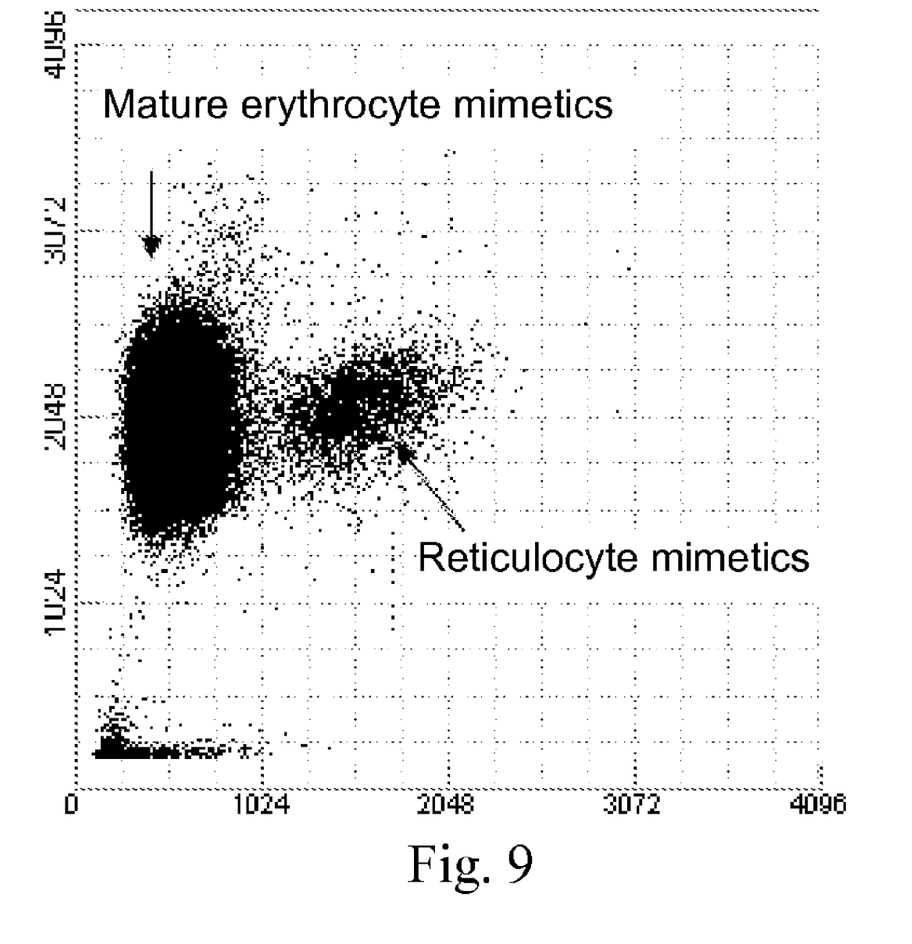
FIG. 9 shows a diagram of a whole blood reference control for use in a hematology analyzer formulated by mixing the reticulocyte mimetics prepared in Example 8 in a certain proportion with other blood cell mimetics, being detected on the blood cell analyzer whose principle of detection is based on fluorescent staining of nucleic acids (only RET channel is shown), wherein the abscissa represents fluorescence intensity and the ordinate represents forward scattered light intensity.

Fresh anticoagulant human whole blood was collected. The anticoagulant whole blood was centrifuged at 2400 rpm for 5 minutes. The supernatant was discarded and the pellet was washed with washing solution followed by further centrifugation at 2400 rpm for 5 minutes. Washing was repeated for one or two times. The supernatant was discarded, and the leukocytes were removed using a leukocyte filter. The filtrate was adjusted to an erythrocyte concentration of $1\times10^{12}$ cells/L using cell treatment solution A and stirred to homogeneity for 1-5 minutes. Fixing agent B was added to a final concentration of 2% and reaction was allowed for 5 hours at room temperature while the mixture was constantly stirred to homogeneity. The reaction product was repeatedly washed with washing solution for three or four times. The product was suspended in a suitable amount of preserving solution, and the suspension was mixed in a certain proportion with other cell mimetics to formulate a hematology reference control for a blood analyzer, as described in the foregoing Section "Formulation of Full-Component Reference Controls". The reference control obtained was detected on the blood cell analyzer whose principle of detection is based on fluorescent staining of nucleic acids. The result is as shown in FIG. 9 (only the diagram on the RET channel is shown).

It can be seen from the accompanying Figures that the hematology reference controls formulated in the examples according to the present disclosure, when detected on the blood cell analyzer, will give the reticulocyte area having distinct boundaries from the mature erythrocyte area. Therefore, by virtue of the examples according to the present disclosure, the quality control of reticulocyte count can be achieved.

All data, diagrams, instruments, reagents and steps described herein shall be understood to be illustrative rather than limiting. Although the present disclosure has been described with reference to the above particular embodiments, many modifications and other changes will occur to those skilled in the art. All such modifications and other changes are deemed to fall within the spirit and scope of the invention.

The invention claimed is:

1. A method for preparing reticulocyte mimetics, comprising:
    washing an anticoagulant blood sample containing anucleate erythrocytes and separating the anucleate erythrocytes therein to obtain purified anucleate erythrocytes;
    adding a cell treatment solution and a fixing agent to the purified anucleate erythrocytes to treat and fix substances on a surface of and/or inside the anucleate erythrocytes, said cell treatment solution comprising a protein denaturing agent and optionally a permeate agent and/or a surfactant; and
    washing the product obtained.

2. The method according to claim 1, wherein said protein denaturing agent is selected from guanidine hydrochloride, guanidinium isothiocyanate, urea or ammonium sulfate, or any combination thereof.

3. The method according to claim 1, wherein said fixing agent is selected from acetone, oxalaldehyde, pyruvaldehyde, succinaldehyde, glutaraldehyde, paraformaldehyde, formaldehyde or ethanol, or any combination thereof.

4. The method according to claim 1, wherein said permeate agent is selected from dimethylsulfoxide, glycerol, ethylene glycol, propylene glycol, formamide or acetamide, or any combination thereof.

5. The method according to claim 1, wherein said surfactant is selected from:
a quaternary ammonium-type cationic surfactant having the following general formula:

wherein $R_1$, $R_2$ and $R_3$ are each independently selected from hydrogen atom, $C_1$-$C_8$alkyl or $C_6$-$C_{20}$aralkyl; $R_4$ is selected from $C_8$-$C_{18}$alkyl, $C_{8-18}$alkenyl or $C_6$-$C_{18}$aralkyl; X is selected from halogen, sulphate, or sulphonate anions;

an anionic surfactant having the following general formula:

R—SO$_3$Na wherein R is $C_8$-$C_{20}$alkyl; or
a polyoxyethylene-type nonionic surfactant having the following general formula:

R$_1$-A-(CH$_2$CH$_2$O)$_n$—H wherein R1 is selected from H, $C_{1-22}$alkyl or $C_{2-22}$alkenyl; A is selected from —O—, —COO— or -ph-O—; and n is an integer of 10-1000; or combinations thereof.

6. The method according to claim 5, wherein said cationic surfactant is selected from hexadecyl trimethyl ammonium chloride or dodecyltrimethylammonium chloride, said anionic surfactant is sodium dodecyl sulphonate, and said nonionic surfactant is polyethylene glycol.

7. Reticulocyte mimetics prepared by:
washing an anticoagulant blood sample containing anucleate erythrocytes and separating the anucleate erythrocytes therein to obtain purified anucleate erythrocytes;
adding a cell treatment solution and a fixing agent to the purified anucleate erythrocytes to treat and fix substances on a surface of and/or inside the anucleate erythrocytes, said cell treatment solution comprising a protein denaturing agent and optionally a permeate agent and/or a surfactant; and
washing the product obtained.

8. A whole blood reference control, comprising the reticulocyte mimetics according to claim 7.

* * * * *